United States Patent [19]

Tinucci et al.

[11] Patent Number: 4,996,366

[45] Date of Patent: Feb. 26, 1991

[54] PROCESS FOR THE CATALYTIC HYDROFORMYLATION OF OLEFINS

[75] Inventors: Laura Tinucci, Cervignano D'Adda; Edoardo Platone, Asti, both of Italy

[73] Assignee: Eniricerche S.p.A, Milan, Italy

[21] Appl. No.: 468,855

[22] Filed: Jan. 23, 1990

[30] Foreign Application Priority Data

Jan. 27, 1989 [IT] Italy ............................ 19225 A/89

[51] Int. Cl.$^5$ .............................................. C07C 45/50
[52] U.S. Cl. ................................... 568/454; 568/451; 568/455
[58] Field of Search .................... 568/451, 454, 455

[56] References Cited

U.S. PATENT DOCUMENTS

| | | | |
|---|---|---|---|
| 4,159,999 | 7/1979 | Stauterberger et al. | 568/454 |
| 4,200,592 | 4/1980 | Hignett et al. | 568/454 |
| 4,248,802 | 2/1981 | Kuntz | 568/454 |
| 4,668,824 | 5/1987 | Jenck et al. | 568/454 |
| 4,808,756 | 2/1989 | Tokitoh et al. | 568/454 |

Primary Examiner—Werren B. Lone
Attorney, Agent, or Firm—Hedman, Gibson, Costigan & Hoare

[57] ABSTRACT

Process for the catalytic hydroformylation of olefins in which an olefin is reacted with hydrogen and carbon monoxide, with the process being carried out by operating in a liquid, aqueous-organic reaction medium, in the presence of a water-soluble complex catalyst containing a metal active in the hydroformylation, wherein said aqueous-organic medium is in the form of a microemulsion consituted by an oil phase, an aqueous phase, a surfactant and a co-surfactant, with said oil phase constituting the external phase of said microemulsion, and said aqueous phase constituting the internal phase of said microemulsion.

17 Claims, No Drawings

PROCESS FOR THE CATALYTIC HYDROFORMYLATION OF OLEFINS

The present invention relates to a process for the catalytic hydroformylation of olefins with hydrogen and carbon monoxide, which uses a liquid reaction medium in microemulsion form.

The hydroformylation, also said "oxosynthesis", constitutes an important industrial process for the production of aldehydes and/or alcohols from olefins, carbon monoxide and hydrogen. The products obtained from hydroformylation are raw materials used in large amounts in various sectors in the art. The hydroformylation catalysts, generally used for the intended purpose, are cobalt-based catalysts and rhodium-based catalysts, and in particular rhodium-based catalysts containing rhodium complexed with a phosphinic ligand. For further information about this prior art, reference is made in particular to the description contained in "New Synthesis with Carbon Monoxide", Ed. J. Falbe, Springer-Verlag Berlin, Heidelberg, New York 1980, Chapter 1.

One of the drawbacks which affect the processes of hydroformylation known from the prior art, which are carried out in an homogeneous organic phase with oil-soluble catalysts, consists in the difficulties to be coped with in the separation and recovery of the catalyst from the reaction mixture of hydroformylation, a matter of fact which constitutes a serious problem, also on considering the cost of the catalyst.

A solution proposed in order to solve this problem consists in carrying out the reaction of hydroformylation in a mixed aqueous-organic medium, in the presence of an aqueous solution of a water-soluble complex catalyst of rhodium, such as, e.g., the complexes obtained from rhodium metal or from a compound of rhodium and a water-soluble sulfonated triarylphosphine, as disclosed in U.S. Pat. No. 4,248,802. By operating in this way, at the end of the reaction of hydroformylation an organic phase—which contains the reaction products—can be separated from an aqueous phase, which contains the catalyst. Unfortunately, the reaction of hydroformylation carried out in a mixed medium requires the adoption of very high pressures and of long reaction times, in particular in case higher olefins are used, a fact which is not very attractive from an industrial viewpoint.

In order to render milder the hydroformylation conditions, it was proposed in the past that a mixed aqueous-organic medium should be used, with a reactant being incorporated in said mixed reaction medium, which reactant, endowed with characteristics of affinity for both the aqueous phase and the organic phase, is constituted by a phase-transfer agent or a surfactant agent, as disclosed, e.g., in French Pat. No. 2,489,308. However, the results which can be obtained by means of the adoption of such phase-transfer agents or surfactant agents, have not been shown to be at all satisfactory yet.

The present Applicant has found now that the drawbacks which affect the prior art, as hereinabove mentioned, can be overcome by carrying out the reaction of hydroformylation of the olefins in an aqueous-organic medium and with a water-soluble complex hydroformylation catalyst, with such an aqueous-organic medium being maintained in the form of a microemulsion, at least during a substantial portion of the hydroformylation reaction time. In particular, the present Applicant was able to find that when the process of hydroformylation is carried out in a microemulsion system, extremely mild conditions can be adopted, also in case of long-chain olefins, with high values of yield and selectivity to the useful reaction products being attained. The present Applicant could also find that such an operating modality makes it possible the catalyst to be easily and completely separated at the end of the hydroformylation reaction.

In accordance therewith, the present invention relates to a process for the catalytic hydroformylation of olefins by means of the reaction of an olefin with hydrogen and carbon monoxide, which process is carried out by operating in a liquid, aqueous-organic reaction medium, in the presence of a water-soluble complex catalyst containing a metal active in the hydroformylation, characterized in that said aqueous-organic medium is, during at least a substantial portion of the hydroformylation reaction time, in the form of a microemulsion containing an oil phase, an aqueous phase, a surfactant and a co-surfactant, with said oil phase constituting the external phase and said aqueous phase constituting the internal phase of said microemulsion.

In the present invention, by "microemulsion" a fluid, single-phase, isotropic composition, i.e., a homogeneous liquid system, is meant, which is constituted by an olefin, or by an olefin and its hydroformylation products, as the external, oil phase; an aqueous solution of the water-soluble complex catalyst, as the internal phase; a surfactant and a co-surfactant. In particular, in said microemulsion the size of the particles of the internal phase is smaller than one fourth of the wave length of visible light, i.e., is smaller than about 1,400 Å, and is comprised in general within the range of from 75 to 1,200 Å. This microemulsion spontaneously forms when the constituents thereof are simply mixed with one another at the beginning of the reaction of hydroformylation and remains unexpectedly stable over at least a substantial portion of the hydroformylation reaction time, under the typical reaction conditions, as the olefin is gradually replaced by the products of its hydroformylation.

In this way, it results it possible the reaction of hydroformylation to be carried out under conditions of intimate contact of the reactants with one another, which makes it possible high yields of useful reaction products to be obtained by operating under mild conditions of temperature and pressure, and within industrially useful times. The present Applicant found also that the microemulsion tends to break spontaneously when the conversion of the olefin reaches high values, with an oil phase containing the hydroformylation products, and an aqueous phase containing the complex catalyst being produced. In that way, the substantially complete recovery of the catalyst as an aqueous phase, and the direct recycling of such a solution into the hydroformylation reaction become possible.

By means of the term "over at least a substantial portion of the hydroformylation reaction time", it is herein meant that the reaction medium will remain in its microemulsion form up to a conversion of at least 50%, and preferably of at least 70%, of the olefin into the relevant hydroformylation products.

The olefins which can be submitted to the process according to the present invention are either linear or branched alpha-olefins or internal olefins, generally containing from 5 to 24 carbon atoms. Examples of these olefins are 1-pentene, 1-octene, 1-dodecene, 1-tetradecene, 1-hexadecene, 1-eicosene, 2-hexene, 4-decene, 5-dodecene, 7-tetradecene and 9-eicosene. Preferably olefins are submitted to the hydroformylation, which contain from 9 to 20 carbon atoms. Of course, also mixture constituted by a plurality of olefins can be hydroformylated as well.

In case oa linear alpha-olefins, the process according to the instant invention makes it possible aldehydes and/or alcohols with a high content of the linear isomer as compared to the branched isomer to be obtained, in particular when rhodium-based catalysts are used.

The complex catalyst useful for the purposes of the present invention is a water-soluble catalyst formed by a metal active in the hydroformylation, or by a compound or a complex compound of such a metal, and a water-soluble phosphinic ligand. The metals active in the hydroformylation can be generally selected from among the transition metals. Among these cobalt, ruthenium, rhodium, osmium, iridium and platinum are preferred. Rhodium is the most preferred one. The compounds or complexes of the transition metals can be selected from among those which are normally used in the art, such as rhodium acetylacetonate dicarbonyl, rhodium trichloride trihydrate, bis-(rhodium chloride 1,5-cyclooctadiene), [rhodium-bis-(1,5-cyclooctadiene)] tetraphenylborate or tetrafluoroborate, [dirhodium trihydroxy bis-(p-cymene or hexamethylbenzene)] tetraphenylborate or tetrafluoroborate, [palladium allyl (1,5-cyclooctadiene)] tetraphenylborate or tetrafluoroborate, dipalladium tris(dibenzylidene acetone), dipotassium palladium tetrachloride, dipotassium platinum tetrachloride, ruthenium trichloride trihydrate, dipotassium ruthenium hexachloride and diruthenium tetrachloride bis-(p-cymene or hexamethylbenzene).

The water-soluble phosphinic ligands are normally selected from among the sulfonated phosphines and in particular from among the sulfonated triarylphosphines. Among the sulfonated triarylphosphines, the triphenylphosphine sulfonates bearing from 1 to 5 sulfonic groups, and preferably 3 sulfonic groups on their phenyl rings, are preferred. Such sulfonic groups shall be suitably salified, in particular as alkali-metal or ammonium salts. Furthermore, the phenyl groups can bear further substituents, in addition to the sulfonic group, which do not negatively interfere with the hydroformylation reaction. Examples of such further substituents are the alkyl, alkoxy, halogen, hydroxy, cyano, nitro and alkylamino groups. The sulfonated triarylphosphines are products known in the art, and some processes for preparing them are reported, e.g., in U.S. Pat. Nos. 4,668,824; 4,483,801; and 4,483,802; and in European patent application publ. No. 158,572. In the process according to the present invention, as the phosphinic ligand, the trisodium salt of tri-(m-sulfophenyl)-phosphine is preferably used.

The complex hydroformylation catalysts are prepared by simply putting the transition metal, or a compound, or a complex thereof, into contact with the water-soluble phosphinic ligand in an aqueous medium. The water-soluble phosphinic ligand should advantageously be present in excess over the necessary stoichiometric amount for forming the complex hydroformylation catalyst, and, in particular, from more than 1 mol up to 100 mol of phosphine, and preferably from 2 mol up to 10 mol of phosphine, are used per each mol of metal active in the hydroformylation, or of the compound or complex of such a metal.

The surfactant used in the microemulsion according to the present invention is suitably selected from among the oil-soluble surfactants of anionic and non-ionic type.

In particular, the anionic surfactants can be selected from among the carboxylates, the sulfonates, the sulfates of the alkali-metals, or of ammonium. Examples of carboxylate surfactants are the metal soaps with

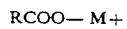

structure, wherein R is a linear hydrocarbon chain containing from about 9 to about 20 carbon atoms. Examples of sulfonated surfactants are the alkylbenzenesulfonates containing, on the average, about 12 carbon atoms in their alkyl group, the alkylarene-sulfonates, the lignin-sulfonates, the naphthalene-sulfonates, the sulfonated alpha-olefins and petroleum sulfonates. Examples of sulfate surfactants are the sulfated alcohols, the sulfated alcohol ethoxylates, the sulfated alkylphenol ethoxylates, the sulfated esters, acids, and amides, the sulfated oils and fats of natural origin.

Furthermore, the non-ionic surfactants can be selected from among the alcohol ethoxylates, the alkylphenol ethoxylates, the esters of carboxy acids, the esters of glycerol, the polyoxyethylene esters, the ethoxylates of fats, oils and waxes of natural origin, the glycol esters of fatty acids, the amides of carboxy acids and the block copolymers of alkylene oxides.

Advantageously, the anionic or non-ionic surfactant used for the microemulsion will have an HLB value (hydrophile-lipophile balance) lower than about 10.

Specific examples of surfactants useful in the microemulsions according to the present invention are sodium dodecylbenzenesulfonate, sodium bis-(2-ethylhexyl)-sulfo-succinate, sodium caprylate, sodium miristate and the polyethoxy alcohol carboxylates, such as, e.g., those as reported in U.S. Pat. No. 4,607,121.

The co-surfactant used in the microemulsion according to the present invention is advantageously selected from among the monohydroxy aliphatic alcohols containing from 3 to 7 carbon atoms in their molecule, and in particular the linear-chain alcohols belonging to this class, with the most preferred ones being n-butanol and n-pentanol.

The microemulsion according to the present invention is obtained by simply putting the olefin, the aqueous solution of the water-soluble complex catalyst, the surfactant and the co-surfactant into contact with one another according to a whatever sequence of addition. Such a microemulsion will advantageously contain
 from 20 to 80% by weight of olefin,
 from 5 to 30% by weight of the aqueous solution of the catalyst,
 from 5 to 30% by weight of surfactant, and
 from 10 to 50% by weight of the co-surfactant.

Furthermore, the concentration of the complex catalyst in the aqueous solution will be comprised within the range of from 1 to 10 g/liter.

According to the preferred form of practical embodiment of the present invention, the olefin content in the microemulsion will be comprised within the range of from 50 to 70% by weight, the content of the aqueous solution of the catalyst will be comprised within the range of from 5 to 10% by weight, the content of surfactant will be comprised within the range of from 5 to 10% by weight, and the content of co-surfactant will be comprised within the range of from 15 to 30% by weight. Furthermore, in the preferred form of practical embodiment of the present invention, said aqueous solution will contain from 3 to 7 g/liter of complex catalyst.

Such a microemulsion is highly stable under the hydroformylation conditions, which are stated in the following, during a substantial portion of the hydroformylation time, i.e., until high values (higher than at least 50% and generally higher than about 70%) of conversion of the olefin into the relevant hydroformylation products are reached. The oil phase of the microemulsion is thought to be constituted during the course of the hydroformylation by the not yet transformed olefin and by the relevant hydroformylation products.

The present Applicant was also able to find that when the unreacted olefin is nearly exhausted, the microemulsion tends to break generating an aqueous phase containing the water-soluble complex catalyst and a portion of the co-surfactant; and an oil phase containing the hydroformylation products, together with the unreacted olefin and the residual portion of the cosurfactant. When this occurs, the two phases can be separated, and the aqueous phase can be directly recycled to the reaction and the products of hydroformylation can be recovered from the oil phase.

In case the reaction medium is still in the microemulsion form at the end of the hydroformylation process, the microemulsion can be broken by means of the simple addition of water and/or of the co-surfactant, so as to bring the system out of the range of stability of the microemulsion, and cause the microemulsion to break into the desired two phases.

The reaction of hydroformylation can be carried out according to a continuous process, or batchwise, with a mixture of hydrogen and carbon monoxide being fed to the liquid reaction medium in microemulsion form, operating at a temperature which can be generally comprised within the range of from 70° to 150° C., and under a pressure comprised within the range of from 3 to 100 bar. The molar ratio of hydrogen to carbon monoxide contained in the gas stream fed to the reaction can be generally comprised within the range of from 1:1 to 5:1.

The preferred reaction conditions are: a reaction temperature comprised within the range of from 75° to 90° C., a reaction pressure comprised within the range of from 10 to 40 bar and a molar ratio of hydrogen to carbon monoxide in the gas stream fed to the reaction, of the order of 1:1. Under these conditions, the reaction times are typically of the order of from 1 to 10 hours.

By operating under these conditions, high transformation rates of the olefin into the relevant hydroformylation products are obtained, with high values of yield and of selectivity to the useful reaction products. These useful reaction products will be basically constituted by aldehydes in case equimolecular amount of hydrogen and carbon monoxide are used, whilst in case an excess of hydrogen is contained in the reaction mixture, the respective alcohols will be formed. When alpha-olefins are used as the reactants, high ratios of the linear isomer to the iso isomer are obtained in the useful reaction products. At higher reaction temperatures, and with low values of hydrogen to carbon monoxide ratio, small amounts of acetalic products—deriving from the interaction between the aldehyde and the co-surfactants—can be formed in addition to the free aldehyde. Also these acetalic products are useful reaction products, in that they can be transformed into aldehydes by acidic hydrolysis, or they can be hydrogenated in order to yield the relevant alcohol together with the free aldehyde. This latter treatment is preferred, in that the alcohol generally constitutes the desired end product, at least in case of long-chain reaction products.

In the following experimental examples, which are reported in order to better illustrate the present invention, the following general procedure is followed. The reactions are carried out in a HOFER autoclave of 250 ml of capacity, made from AISI 316 L, equipped with magnetic-drive stirring means. The reactants are charged to the autoclave, a tightness test is carried out with nitrogen up to a pressure of 35 bar, the autoclave is purged seven times with nitrogen at 10 bar, and nitrogen is removed by means of a mixture of hydrogen and carbon monoxide in the ratio of 50:50 by volume, with said autoclave being pressurized twice. The pressure is then adjusted at the reaction pressure value, and the contents of the autoclave are heated up to the desired temperature. At the end of the reaction time, the autoclave is cooled down to room temperature, the reaction mixture is discharged after purging the reaction vessel five times with nitrogen, and the reaction mixture is submitted to gas-chromatographic analysis.

EXAMPLE 1

By operating at room temperature, 60 g (0.356 mol) of n-dodecene-1 (a product by Shell company), 21.3 g of n-butanol, 5.0 g (0.017 mol) of sodium n-dodecylsulfate and 6 g of an aqueous solution containing 30 g/liter of the trisodium salt of tris-(m-sulfophenyl)phosphine and 5 g/liter of bis(rhodium chloride-1,5-cyclooctadiene) [(1,5-cyclooctadienyl) dirhodium-(I) dichloride (a product available from the market)]are mixed with one another in a whatever order, by operating at room temperature. A microemulsion forms spontaneously, which has the following composition (as percentages by weight):

| | |
|---|---|
| n-dodecene-1 | 65.0% |
| n-butanol | 23.0% |
| sodium n-dodecyl sulfate | 5.4% |
| and | |
| aqueous solution of catalyst | 6.6% by weight |

In particular, the aqueous solution contains 30 mg of complex catalyst and the molar ratio of the trisodium salt of (m-sulfophenyl)phosphine to bis-(rhodium chloride-1,5-cyclooctadiene) is of 5:1.

The formation of the microemulsion is confirmed by the study of the phase diagram and by the Molecular Self Diffusion, as determined by means of Pulsed Gradient NMR Spectroscopy. The so obtained microemulsion is charged to the autoclave, the pressure inside the autoclave is increased uo to 40 bar with a mixture of hydrogen and carbon monoxide in the ratio of 1:1 by volume, the contents of the autoclave are heated up to 75° C. and are kept 9 hours at this temperature, with stirring. At the end of this time period, the autoclave is cooled down to room temperature and the reaction mixture is discharged. The so obtained reaction mixture is in the form of two phases, i.e., an upper oil phase containing n-tridecanal, iso-2-methyldodecanal, besides unaltered n-dodecene-1 and a portion of n-butanol co-surfactant; and a lower aqueous phase containing the catalyst and the balance of the co-surfactant.

From the gas-chromatographic analysis of the oil phase, the conversion of the olefin is determined to be of 92.05%, with a conversion into aldehyde (both the normal and the iso isomers) of 90.2% by mol. The selectivity to aldehyde results hence to be of 98.0% by mol. The molar ratio of the normal isomer to the iso isomer of the aldehyde is of 1.97.

To the aqueous phase recovered, which practically contains all of the catalyst, 20 g of n-butanol and 60 g of n-dodecene-1 are added in order to form again the microemulsion. This latter is submitted to a second cycle of hydroformylation under the above specified conditions, and results are obtained, which are similar to those as of the first cycle.

EXAMPLE 1

(Comparative Example)

The process is carried out in the same way as of Example 1, but with the co-surfactant being omitted from the reactant mixture. In this way, a microemulsion does not form, and the process is carried out in a reaction medium of emulsion type.

Under these conditions, under a pressure of 40 bar, with a reaction temperature of 75° C., and with a reaction time of 9 hours, the conversion of the olefin is of 71.60%, with a yield to (both normal and iso) aldehyde of 62.0% by mol. Therefore the selectivity to aldehyde results to be of 86.6% by mol. The molar ratio of the normal isomer to the iso isomer of the aldehyde is of 2.55.

EXAMPLE 3

The process is carried out in the same way as of Example 1, at a pressure of 40 bar, a temperature of 95° C., and with a reaction time of 6 hours.

Under these conditions, the conversion of the olefin is of 92.5%, with a yield to both normal and iso) aldehyde of 82.7% by mol. Therefore the selectivity to aldehyde results to be of 89.4% by mol. The molar ratio of the normal isomer to the iso isomer in the aldehyde is of 1.86. The presence of acetalic compounds is detected in the reaction mixture.

EXAMPLE 4

(Comparative Example)

The process is carried out in the same way as of Example 3, but with the co-surfactant being omitted from the reactant mixture. In this way, a microemulsion does not form, and the process is carried out in a reaction medium of emulsion type.

Under these conditions, with a pressure of 40 bar, a temperature of 95° C., and a reaction time of 6 hours, a conversion of 52.8% of the olefin is obtained, with a yield to (both normal and iso) aldehyde of 46.4% by mol. Therefore the selectivity to aldehyde results to be of 87.9% by mol. The molar ratio of the normal isomer to the iso isomer in the aldehyde is of 2.27.

EXAMPLE 5

The process is carried out in the same way as of Example 1, at a pressure of 10 bar, a temperature of 75° C., and with a reaction time of 9 hours.

Under these conditions, the conversion of the olefin is of 85.2%, with a yield to (both normal and iso) aldehyde of 79.2% by mol. Therefore the selectivity to aldehyde results to be of 93.0% by mol. The molar ratio of the normal isomer to the iso isomer in the aldehyde is of 2.91.

EXAMPLE 6

(Comparative Example)

The process is carried out in the same way as of Example 5, but with the co-surfactant being omitted from the reactant mixture. In this way, a microemulsion does not form, and the process is carried out in a reaction medium of emulsion type.

By operating under a pressure of 10 bar, with a temperature of 75° C., and a reaction time of 9 hours, a conversion of 19.8% of the olefin is obtained, with a yield to (both normal and iso) aldehyde of 13.4% by mol. Therefore the selectivity to aldehyde results to be of 67.7% by mol. The molar ratio of the normal isomer to the iso isomer in the aldehyde is of 2.29.

EXAMPLE 7

The process is carried out in the same way as of Example 1, at a pressure of 40 bar, a temperature of 108° C., and with a reaction time of 4 hours.

Under these conditions, a conversion of the olefin of 93.1% is obtained, with a yield to (both normal and iso) aldehyde of 74.0% by mol. Therefore the selectivity to aldehyde results to be of 79.5% by mol. The molar ratio of the normal isomer to the iso isomer in the aldehyde is of 1.79. The presence of acetalic compounds is detected in the reaction mixture.

EXAMPLE 8

The process is carried out in the same way as of Example 1, at a pressure of 3.5 bar, a temperature of 75° C., and with a reaction time of 9 hours.

Under these conditions, a conversion of the olefin of 34.2% is obtained, with a yield to (both normal and iso) aldehyde of 30.3% by mol. Therefore the selectivity to aldehyde results to be of 88.6% by mol. The molar ratio of the normal isomer to the iso isomer in the aldehyde is of 3.26.

EXAMPLE 9

The process is carried out in the same way as of Example 1, but with n-tetradecene-7 being used instead of n-decene-1.

By operating at a pressure of 40 bar, at the temperature of 109° C., and with a reaction time of 6.5 hours, the conversion, relatively to the olefin, is of 59%, with a selectivity to both normal and iso aldehydes higher than 90%.

EXAMPLE 10

(Comparative Example)

The process is carried out in the same way as of Example 1, but with sodium n-dodecylsulfate being omitted, and a double-phase reaction medium being hence obtained.

Under these conditions, after 9 hours of reaction, the conversion of the olefin is of 6%.

EXAMPLE 11

(Comparative Example)

The process is carried out in the same way as of Example 1, but with sodium n-dodecylsulfate and n-butanol being both omitted, and a double-phase reaction medium being consequently obtained. Furthermore, the reaction temperature is maintained at 100° C. for 3 hours and at 50° C for 14 hours. Under these conditions, the conversion of the olefin is of 10%.

We claim:

1. Process for the catalytic hydroformylation of olefins to produce aldehydes and/or alcohols by means of the reaction of linear or branched alpha-olefins or internal olefins of from 5 to 24 carbon atoms with hydrogen and carbon monoxide, which process is carried out by operating at a temperature ranging from 70° to 150° C. and at a pressure ranging from 3 to 100 bar in a liquid, aqueous-organic reaction medium, in the presence of a water-soluble complex catalyst containing a metal active in the hydroformylation selected from the group consisting of cobalt, ruthenium, rhodium, palladium, osmium, iridium and platinum, characterized in that said aqueous-organic medium is, during at least a substantial portion of the hydroformylation reaction time, in the form of a microemulsion containing an oil phase, an aqueous phase, a surfactant and a co-surfactant, with said oil phase constituting the external phase and said aqueous phase constituting the internal phase of said microemulsion.

2. Process according to claim 1 characterized in that said olefin contains from 9 to 20 carbon atoms.

3. Process according to claim 1, characterized in that said aqueous phase contains dissolved a water-soluble, complex catalyst formed by a water-soluble phosphine and a metal selected from the group consisting of cobalt, ruthenium, rhodium, palladium, osmium, iridium and platinum, a water-soluble compound or a water soluble complex of said metal active in the hydroformylation.

4. Process according to claim 3, characterized in said water-soluble phosphine is a sulfonated phosphine, and preferably is a sulfonated triarylphosphine.

5. Process according to claim 4, characterized in that said sulfonated triarylphosphine is the trisodium salt of tri-(m-sulfophenyl)-phosphine.

6. Process according to claim 3, characterized in that said metal active in the hydroformylation comprises rhodium.

7. Process according to claim 3, characterized in that the complex catalyst contains from more than 1 mol up to 100 mol of phosphine, and preferably from 2 mol up to 10 mol of phosphine, per each mol of metal active in the hydroformylation, or of the compound or complex of such a metal.

8. Process according to claim 3, characterized in that the concentration of the complex catalyst in the aqueous phase is comprised within the range of from 1 to 10 g/liter, and is preferably comprised within the range of from 3 to 7 g/liter.

9. Process according to claim 1, characterized in that said surfactant is an oil-soluble surfactant selected from among the anionic and non-ionic surfactants.

10. Process according to claim 9, characterized in that said anionic surfactant is selected from among the metal soaps, the alkylbenzenesulfonates, the alkylarene sulfonates, the lignin-sulfonates, the naphthalenesulfonates, the sulfonated alpha-olefins, the petroleum sulfonates, the sulfated alcohols, the sulfated alcohol ethoxylates, the sulfated alkylphenol ethoxylates, the sulfated esters, acids, and amides, the sulfated oils and fats of natural origin, the alcohol ethoxylates, the alkylphenol ethoxylates, the esters of carboxy acids, the esters of glycerol, the polyoxyethylene esters, the ethoxylates of fats, oils and waxes of natural origin, the glycol esters of fatty acids, the amides of carboxy acids and the block copolymers of alkylene oxides.

11. Process according to claim 10, characterized in that said surfactant is selected from among sodium dodecylbenzenesulfonate, sodium bis-(2-ethylhexyl)-sulfosuccinate, sodium caprylate, sodium miristate and polyethoxy alcohol carboxylates.

12. Process according to claim 1, characterized in that the co-surfactant is selected from among the mono-hydroxy aliphatic alcohols containing from 3 to 7 carbon atoms in their molecule, and preferably is n-butanol or n-pentanol.

13. Process according to claim 1, characterized in that the microemulsion contains
from 20 to 80% by weight of olefin,
from 5 to 30% by weight of the aqueous solution of the catalyst,
from 5 to 30% by weight of surfactant, and
from 10 to 50% by weight of the co-surfactant.

14. Process according to claim 13, characterized in that said microemulsion contains
from 50 to 70% by weight of olefin,
from 5 to 10% by weight of the aqueous solution of the catalyst,
from 5 to 10% by weight of surfactant, and
from 15 to 30% by weight of the co-surfactant.

15. Process according to claim 1, characterized in that the hydroformylation is carried out at a temperature comprised within the range of from 70° to 150° C., and under a pressure comprised within the range of from 3 to 100 bar, with hydrogen and carbon monoxide being fed in a mutual ratio comprised within the range of from 1:1 to 5:1.

16. Process according to claim 15, characterized in that said reaction temperature is comprised within the range of from 75° to 90° C., said reaction pressure is comprised within the range of from 10 to 40 bar and said molar ratio of hydrogen to carbon monoxide is of the order of 1:1.

17. Process according to claim 1, characterized in that the reaction of hydroformylation is carried out until the microemulsion is broken, and an oil phase, containing the hydroformylation reaction products, and an aqueous phase, containing the hydroformylation catalyst, are formed, with said oil phase being submitted to the treatment for the recovery of the hydroformylation products, and said aqueous phase being recycled to the hydroformylation reaction.

* * * * *